(12) United States Patent
Hurt

(10) Patent No.: US 7,378,242 B2
(45) Date of Patent: May 27, 2008

(54) DNA SEQUENCE DETECTION BY LIMITED PRIMER EXTENSION

(75) Inventor: Richard A. Hurt, Oak Ridge, TN (US)

(73) Assignee: Atom Sciences, Inc., Oak Ridge, TN (US)

( * ) Notice: Subject to any disclaimer, the term of this patent is extended or adjusted under 35 U.S.C. 154(b) by 0 days.

(21) Appl. No.: 11/081,518

(22) Filed: Mar. 17, 2005

(65) Prior Publication Data

US 2005/0239109 A1    Oct. 27, 2005

Related U.S. Application Data

(60) Provisional application No. 60/553,949, filed on Mar. 18, 2004.

(51) Int. Cl.
    *C12Q 1/68*      (2006.01)
    *C12P 19/34*     (2006.01)

(52) U.S. Cl. .......................... 435/6; 435/91.1
(58) Field of Classification Search ................... None
See application file for complete search history.

(56) References Cited

U.S. PATENT DOCUMENTS

| | | | |
|---|---|---|---|
| 6,355,433 B1* | 3/2002 | Xu et al. ................. | 435/6 |
| 2003/0186234 A1* | 10/2003 | Kurn ......................... | 435/6 |
| 2003/0224385 A1* | 12/2003 | Pihan ........................ | 435/6 |
| 2004/0058378 A1* | 3/2004 | Kong et al. .............. | 435/6 |

OTHER PUBLICATIONS

Chung et al., A novel primer-extension assay for the detection of a G to A mutation in the distal precore region of hepatitis B virus DNA. J. Viral Hepatitis (1999) 6: 305-313.*

* cited by examiner

*Primary Examiner*—Young J. Kim
*Assistant Examiner*—David C. Thomas
(74) *Attorney, Agent, or Firm*—Birch, Stewart, Kolasch & Birch, LLP

(57) ABSTRACT

A novel limited primer extension reaction improves detection sensitivity and specificity in a variety of hybridization platforms. In the invention, a sequence of target DNA that lacks one of the four types of nucleic acid bases for a span of eight or more adjacent nucleotide positions is selected for use. This sequence is referred to as the extension complement sequence, or ECS. A primer with a sequence that is complementary to the target sequence that is immediately downstream (to the 3' side) of this ECS is used to initiate an extension reaction. Extension occurs using a DNA polymerase and standard deoxynucleoside triphosphates for three of the four types of nucleic acid bases. The fourth base, which is complementary to the base missing in the ECS, is either absent or present only in the form of a dideoxynucleoside triphosphate, which does not support further extension. In either case, the extension reaction does not proceed past the first occurrence in the template of the base that is missing in the ECS. This results in a primer extension product with fixed length determined by the length of the ECS. The process can be repeated using a thermal-stable polymerase in a thermal-cycled reaction that results in a linear amplification of the targeted sequence. The resulting limited primer extension products serve as ideal hybridization analytes for determination of sample sequence content using microarrays.

24 Claims, 2 Drawing Sheets
(1 of 2 Drawing Sheet(s) Filed in Color)

DNA SEQUENCE DETECTION BY LIMITED PRIMER EXTENSION

This Nonprovisional application claims priority under 35 U.S.C. § 119(e) on U.S. Provisional Application No(s).). 60/553,949 filed on Mar. 18, 2004, the entire contents of which are hereby incorporated by reference.

TECHNICAL FIELD

This invention is related to the field of nucleic acid sequence detection by hybridization. This includes deoxyribonucleic acid (DNA) sequences or cDNA sequences prepared from ribonucleic acid (RNA) targets for a wide range of applications, including: clinical diagnostics, clinical screening, genotyping, pathogen detection, pathogen identification, detection of specific genes, gene expression studies, medical applications, and detection of polymorphisms.

BACKGROUND FOR THE INVENTION

DNA and RNA

Genetic information is contained within the sequence of four bases (adenine [A], guanine [G], thymine [T], and cytosine [C]) in deoxyribonucleic acid (DNA). Similarly, there are four bases in ribonucleic acid (RNA), A, G, C and Uracil (U). In both DNA and RNA, these bases are attached to a sugar-phosphate backbone. This backbone has a structural directionality, with one terminus specified as the 5' end and the other being the 3' end. Unless otherwise specified, DNA sequences are, by convention, written from the 5' end first. Thus, AGA-TCG-GTC is equivalent to 5'-AGA-TCG-GTC-3'. Furthermore, when two single strands of DNA bind (associate) to form double-stranded DNA (duplexed DNA), they do so in an anti-parallel fashion, with the 5' to 3' direction in one strand being 180° from the 5' to 3' direction in the other strand. The most stable hybrids are formed when the sequence in one strand is complementary to the sequence in the other strand. A is complementary to T and G is complementary to C in DNA/DNA duplexes; A is complementary to U and G is complementary to C in DNA/RNA hybrids. This allows sequence information to be obtained about target nucleic acids by testing if stable hybrids form with probe nucleic acids for which the sequence is known. Several parameters, such as the length of the hybrid, degree of complementarity, position of any mismatches, G-C content, pH, and salt concentration all affect the stability of the resulting hybrid.

Primer Extension Reactions

During primer extension, a short sequence of DNA called a primer associates with a complementary sequence on the target DNA and a DNA polymerase uses deoxynucleoside triphosphates (dNTPs) to sequentially add nucleotides to the 3' terminus of the primer using the complementary strand as a template to maintain complementarity of the extended sequence to the target DNA sequence. For extension to occur, a 3' hydroxyl group is required on the furanose ring, which is the sugar moiety of the nucleic acid backbone. If the 3' hydroxyl group of a nucleotide is replaced with a hydrogen atom, the nucleotide is described as a dideoxynucleotide, and cannot support attachment of an additional base during extension with a polymerase. Thus, use of a dideoxynucleoside triphosphate (ddNTP) to incorporate a 2',3' dideoxynucleotide terminates the extension reaction. ddNTP termination of primer extension reactions is well known and is the basis of the Sanger reaction. Another method of terminating the extension is to have one or more of the dNTPs absent in the reaction. When the extension reaction reaches a point where complementary extension requires the missing dNTP, the reaction will either stop or a mismatched extension will occur. Those familiar with the art will recognize that there are other ways to block extension reactions, such as is done in 3'-Azido-3'-deoxythymidine (AZT). Thermal-stable DNA polymerases can be used in the process to allow generation of multiple extension products from the same nucleotide positions on each targeted DNA template.

In the Sanger reaction, the relative concentration of ddNTPs to dNTPs is used to terminate the primer extension reactions. This results in various lengths for the extension products and is significantly different than the fixed-length products of the present invention. A sequence-specific termination of a primer extension reaction similar to that in the present invention was used to detect a G to A mutation in the distal precore region of hepatitis B virus DNA [Chung et al., *J Viral Hepat.* 6(4):305, (1999)] but these researchers did not use the product for hybridization targets.

Hybridization to Immobilized Probes

The use of many different probe sequences targeting multiple genetic loci in a single test is called "multiplexing". Immobilization of these probes onto a solid surface, called a "hybridization array", allows identification of the unique nucleic acid sequences by the known probe position on the surface. Immobilized probes on hybridization arrays (which are sometimes called DNA microarrays, genosensors, gene chips, etc.) are considered by many researchers to be the best method to determine if a specific sequence of DNA or RNA exists in a sample. The probes used in hybridization arrays can be short oligodeoxynucleotides (ODNs), which are typically created by chemical synthesis, or longer sections of DNA, which are typically created by cloning or by duplicating DNA using the polymerase chain reaction (PCR) or other amplification techniques. Information about the sequence of the target nucleic acid is obtained by allowing single-stranded target nucleic acid to hybridize to the probes. Under the proper conditions, which are collectively referred to as the "stringency", the existence of a stable hybrid at a particular probe site after hybridization indicates the existence of a complementary sequence in the target nucleic acid. Thus, under the appropriate stringency, the existence of a stable DNA/DNA hybrid at the site of a probe with sequence AGA-TCG-GTC would indicate that a section of the target has the sequence GAC-CGA-TCT. The existence of the stable hybrid is usually determined by attaching a label to the target DNA and detecting that label after the hybridization reaction. Practitioners skilled in the art will recognize that ribonucleic acid (RNA) targets can also be probed by this type of array. Similarly, it will be recognized that the probes may be made from DNA analogs, such as peptide nucleic acids [Egholm et al., U.S. Pat. No. 6,451,968], or chemically modified DNA, such as locked nucleic acids [Petersen and Wengel, *Trends Biotechnol.*, 21: 74 (2003)], which are described below.

Site-specific sequence immobilization in a hybridization array allows a large number of probes to be employed on a single substrate to simultaneously test a target nucleic acid. The advantage of this can be seen in the example of pathogen detection. For pathogen detection and characterization, toxin encoding gene sequences, sequences associated with toxin production and delivery, sequences related to virulence factors, and antimicrobial resistance genes could be targeted simultaneously to improve the certainty of a diagnosis. Diagnosis of viruses would rely on multiple probes that target identifying sequence structures present in the virus genome. The parallel nature of DNA arrays allows control sequences to be tested under identical conditions with the other probes. Control sequences are sequences that are complementary to sequences that are known to be in the target nucleic acid (positive control) or complementary to sequences that are known to be absent in the target nucleic acid (negative control).

Helicase Reactions

Helicases are enzymes that utilize the energy from ATP hydrolysis to unwind double stranded nucleic acids in processes such as replication and recombination where single stranded nucleic acids are required as intermediates [Tackett et al., *Biochemistry*, 40:543-548 (2001)]. DNA helicases exhibit specific polarity defined by the direction of helicase movement on the initially bound DNA strand [Tuteja et al., *Eur. J. Biochem.*, 271:1835-1848 (2004)]. In general, helicases bind DNA that is partially duplexed, however RecBCD, SV40 large antigen, and RuvB helicases preferentially bind to double stranded DNA. For the LPE process helicases that prefer a 3' tail (single-stranded region) on the initially bound strand can be used or helicases that prefer a 5' tail can be used. For helicase driven limited primer extension, the primer binds to template and the polymerase synthesizes the extension product. Then the helicase molecule strips the completed LPE product from the template DNA, a new primer binds to the template and the process is repeated. As opposed to thermal dissociation methods, the helicase driven LPE can make a large number of copies using a single reaction temperature. Because reaction kinetics are based on the concentration of helicase, polymerase, nucleotides and additives, a vast number of LPE products are produced. For longer primers in the LPE reaction, it may be useful to use thermally stable helicases that can withstand temperature needed for high stringency association of primers to the template.

Other Nucleic Acids

Peptide Nucleic Acid (PNA), [Egholm et al., U.S. Pat. No. 6,451,968] is a synthetic analog of DNA that has been used successfully as a replacement for DNA in hybridization and polymerase chain reaction technologies [see Ganesh et al., *Current Org. Chem.*, 4 (9):931 (2000)]. PNA/DNA duplexes and PNA/RNA duplexes are generally more stable than are the corresponding DNA/DNA or DNA/RNA duplexes [Jensen et al., *Biochemistry*, 36:5072 (1997)]. A number of chemical backbone modifications of PNA have been prepared with varying success as to their ability to mimic DNA in hybridization technologies [Ganesh et al., *Current Org. Chem.*, 4(9): 931 (2000)]. The structure of the PNA backbone does not allow standard enzymatic ligation techniques but chemical methods have been developed. Another modification to native nucleic acids involves linking the 2' oxygen and 4' carbon in the sugar backbone. The product of this modification has been named "locked nucleic acid" or LNA. The furanose ring of LNA is locked in a C3'-endo conformation, and this leads to extremely stable LNA/DNA and LNA/RNA duplexes [Petersen and Wengel, *Trends Biotechnol.*, 21: 74 (2003)].

SUMMARY OF THE INVENTION

The present invention is drawn to a limited primer extension (LPE) reaction used to produce short DNA extension products from a targeted template nucleic acid which comprises:

generating extension products having a primer portion and an extension portion, wherein the extension portion are complementary to an extension complement sequence (ECS) in the template DNA that lacks one of the four nucleotides over a span of eight or more nucleotides;

terminating the extension reaction by either the absence of the dNTP that incorporates the nucleotide that is complementary to the nucleotide absent in the ECS or by incorporation of a nucleotide analog that is complementary to the nucleotide absent in the ECS and incapable of supporting further extension; and identifying the extension products by hybridization to a probe immobilized onto a surface followed by detection of the extension product associated to the probe; wherein the probe has sequence identical to, or a subset of, or a superset of, a sequence in the target that includes the ECS.

BRIEF DESCRIPTION OF THE DRAWINGS

The patent or application file contains at least one drawing executed in color. Copies of this patent or patent application publication with color drawing(s) will be provided by the office upon request and payment of the necessary fee.

FIG. 1A (SEQ ID NOS:32 & 2) shows limited Extension. Primer sequences are introduced into a thermal-cycled repetitive limited extension reaction. Primer sequences bind to target DNA immediately 3' to a span of template DNA that lacks one of the four nucleosides. Extension is terminated with the incorporation of a labeled dideoxynucleoside triphosphate. FIG. 1B (SEQ ID NOS:3 & 1) shows Hybridization. The limited primer extension reaction products are hybridized with an array of immobilized probes that are complementary to the extension sequences.

DETAILED DESCRIPTION OF THE INVENTION

Figure 1:
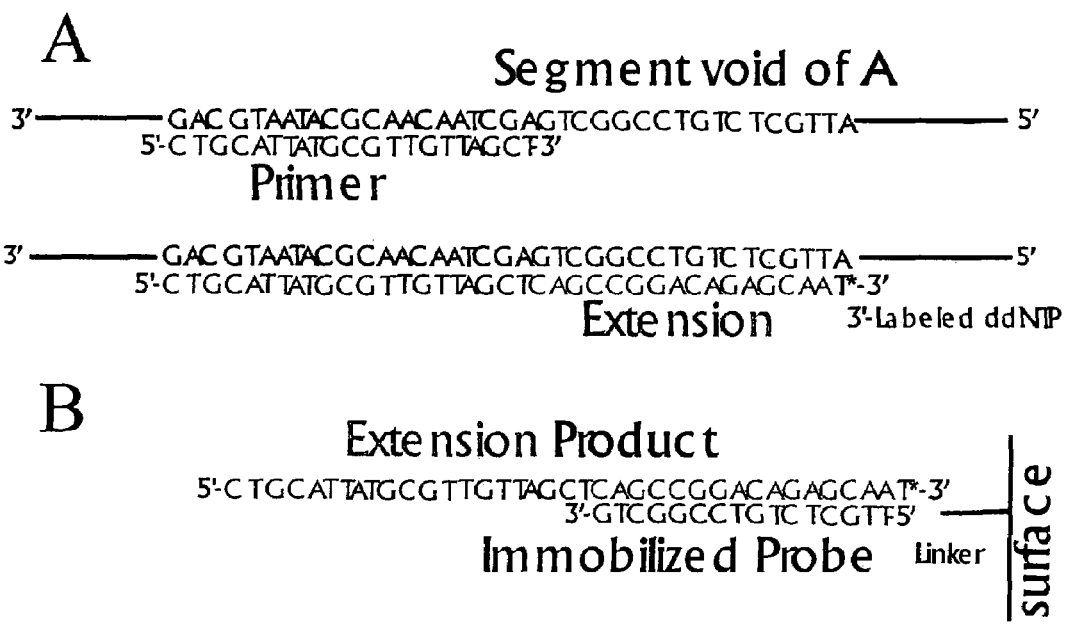
FIG. 1 is a schematic representation of the two-step process for a specific sequence using one embodiment of the invention.

Limited Primer Extension (LPE) has a number of properties that provide advantages over direct labeling methods, or procedures based on the PCR. These include:

The absence of chain reaction products and allows massive multiplexing.

A short sequence is created for hybridization to probes.

Thermal cycling or helicase reactions can be used to achieve a non-exponential, selective target sequence amplification.

Because the amplification always occurs in one direction only, there is no reaction product to compete with association of the product to probes.

When used to generate sequences for hybridization on microarrays, specificity arises not only from the requirement of complementarity for association of primer with the target, but also from the requirement for complementarity for association of the newly synthesized extension product with the immobilized probe.

Some of the advantages that result from these properties include:

Sample multiplexing. The capacity for multiplexing PCR reactions is limited, and simultaneous examination of a sample for a large number of target DNA sequences would require a large number of separate reactions. The invention offers the potential for parallel examination of a large number of targeted sequences in a single set of four reaction tubes, one tube for each combination of three dNTPs with one ddNTP. Because chain elongation terminates following the terminal addition of a dideoxynucleotide after a short elongation, no chain reaction products are generated. In the absence of chain reaction product formation, extension reactions can be multiplexed to a great extent. Many LPE primers can be combined onto a single reaction because; 1) the brevity of the extension yields a high copy number of LPE products before extension reaction components become depleted, and 2) miss-priming events do not yield propagated chain reaction products.

Signal retention: The invention overcomes the difficulty of hybridizing long nucleic acid fragments to short immobilized probes [Southern et al., *Nature Genetics* 21: 5 (1999)]. Those experienced in the art will recognize that association of short ODNs (in this case, the extension reaction products) to immobilized short ODN probes works well, whereas hybridization of a complementary sequence embedded in a long stretch of DNA to a short immobilized ODN is problematic.

Secondary structure: Secondary structure caused by self-association in long single-stranded nucleic acids can inhibit association of probes or primers. The problem with primer association is countered by the use of thermal cycling with high stringency. This opens positions of secondary structure in target nucleic acid and makes them available for primer annealing at each cycle [Baharaeen, et al., *Can. J Microbiol.* 29:546; Bruice and Lima *Biochemistry* 36:5004 (1997)]. However, most conventional DNA amplification methods result in long products that can contain significant secondary structure, resulting in poor hybridization to probes. The short products of the LPE invention are less likely to contain self-complementary regions that cause secondary structure.

Target flexibility. The choice of target for the assay can depend on the nature and condition of the test sample. Because the LPE reaction in the invention can use a thermal-cycling program similar in some respects to that used in the PCR, the targeted sample can consist of double-stranded DNA (dsDNA), single-stranded DNA (ssDNA), or complementary DNA (cDNA).

Improved sensitivity over direct hybridization: Current techniques that involve purification of DNA or RNA followed by labeling using procedures such as random primer extension, nick translation, or random primed reverse transcription, are not sensitive enough for many applications. The invention improves sensitivity over these direct labeling techniques by producing a large number of the LPE products This is accomplished either by using repeated thermal cycles to associate the primer, create the extension product, and then separate the LPE product from the template or by the use of helicases to separate the LPE product and template. Even though primer association and the extension reaction perform optimally at slightly different temperatures, they both perform adequately at an intermediate temperature. However, thermal dissociation requires a higher temperature and a temperature cycle must be used to permit primer association and extension to occur again following thermal dissociation. The helicase technique is especially attractive because a single temperature can be used for all three processes, thus enabling isothermal LPE target amplification. The specificity of the amplification in both cases is due to the fact that the primer sequence must first anneal to the target at high stringency. In addition, the requirement that the resulting extension product must be complementary to an immobilized probe for association to occur further reduces unwanted nonspecific signal.

Quantitative results: The invention yields a quantitative determination of target sequences because of the linear increase in labeled extension reaction products. During the PCR, the exponential increase in prepared template results in excessive consumption of reaction components such as nucleotides and primers [Morrison and Gannon, *Biochemica et Biophysica Acta* 1219:493 (1994); Stolovitzky and Cecchi, *Proc. Natl. Acad. Sci. USA* 93:12947 (1996)]. As this consumption of reaction components approaches exhaustion a plateau effect occurs making quantitative interpretation of the reaction outcome impossible unless a specific analysis such as quantitative competitive PCR (QCPCR) is used. The quantitative attributes of the process described here derive from the non-exponential increase in signal produced by the limited extension reaction.

The invention is a limited primer extension (LPE) reaction designed to provide highly parallel and selective target amplification coupled with microarray hybridization of the LPE products for identification, detection, or characterization of targeted DNA sequences in a DNA sample. The LPE system is an innovative two-step process. The first step requires a sequence, herein called the extension complement sequence (ECS), of eight or more nucleotides in the target nucleic acid that contains only three of the four bases, A, G, C, or T. A primer is selected that is complementary to the section of the target that is immediately adjacent to this sequence at the 3' end. The extension reaction is initiated by adding a polymerase and dNTPs for the three bases that are complementary to the three bases present in the ECS. The fourth nucleoside triphosphate is either absent or present in only the 2',3' dideoxy form (ddNTP). If the fourth dNTP is absent, the extension reaction is essentially terminated by the lack of a dNTP that can continue formation of the complementary LPE target. While it is possible for the extension reaction to continue with incorporation of a mismatched base, this is an inefficient process that would rarely occur on the timescales that will be used for the LPE reaction. The use of a ddNTP for the fourth base would eliminate any chance of a mismatched extension.

The extension reaction product can be dissociated from the template by raising the temperature of the reaction mixture or by incorporating the appropriate helicase into the LPE reaction mixture. In either case, once the LPE product has been separated from the template, it is possible to repeat the entire process. Multiple temperature cycles can be used to amplify the extension product in a near-linear fashion with the number of cycles. In this case, different temperatures could be used for the three steps; association of the primer to the template, extension, and separation of the LPE product from the template. For helicase driven LPE product amplification, a single temperature could be used for these three steps and the amplification would be near-linear with time as long as the primer concentration was much larger than the product concentration.

The second step in the invention involves hybridizing the short LPE reaction products to an array of immobilized probes. In the preferred embodiment, probe sequences immobilized on the microarray are identical to the ECS sequence in the target so that they are complementary to the extension part of the extension product. More generally, the probe sequences may each be any sequence that contains at least a subset of one of the targeted ECS regions or they may extend beyond the targeted ECS region. For example, it may be useful to have probe sequences that complement the extension portion of the LPE product and a portion of the primer. However, extended overlap with the primer sequence complement could cause the primers to associate with the probes.

Because the extension products are short, a prolonged extension is not needed if thermal cycling is used. Rapid cycling between the annealing temperature and the dissociation temperature without pause reduces the time requirement for thermal cycling and is an important consideration for both practical and experimental reasons. Calculation of the $T_d$ for several 40-mer oligonucleotides having 50% (G+C) showed that duplexes of suitable length for LPE products (30-40 bases) typically have a thermal dissociation temperature of approximately 80° C. Therefore rapid cycling between 60 and 80° C. is suitable for single-stranded templates such as cDNA. A standard 94° C. dissociation temperature is required for long dsDNA templates on a limited number of cycles (eg. every $10^{th}$ cycle).

FIG. 1 is a schematic representation of the two-step process for a specific sequence using one embodiment of the invention. A section of DNA is selected that is lacking one of the four bases, in this case, a 16-base segment lacking adenine. This sequence in the target that is lacking a specific base is called the extension complement sequence (ECS). In FIG. 1A, the ECS is 3'-GTC-GGC-CTG-TCT-CGT-T-5' (5'-3' SEQ ID NO:1). A primer is used that is complementary to the sequence adjacent to the ECS on the 3' end. In FIG. 1A, a 21-base primer is used, 5'-CTG-CAT-TAT-GCG-TTG-TTA-GCT-3' (SEQ ID NO:2). For the preferred embodiment of the extension reaction, ddNTP for the base complementary to the base missing in the ECS, and dNTPs for the other three bases are combined with other reagents. For the example shown, a solution of 5'-CTG-CAT-TAT-GCG-TTG-TTA-GCT-3' (SEQ ID NO:2) primers would be combined with sample DNA, thermal-stable polymerase, and a mixture of dNTPs for G, C, and A, and ddNTP for thymine in a buffer suitable for the extension reaction. When the primer is annealed to its complementary target sequence in the sample nucleic acid, the polymerase is able to extend the sequence by polymerization of complementary dNTPs. In the example, once the extension reaction has added 16 bases, the next base added will be T in the dideoxy form. This form prevents further extension. The final extension product includes the primer and the extension. In FIG. 1A, the full extension product is (SEQ ID NO:3) 5'-CTG-CAT-TAT-GCG-TTG-TTA-GCT-CAG-CCG-GAC-AGA-GCA-AT-3'

5'-CTG-CAT-TAT-GCG-TTG-TTA-GCT-CAG-CCG-GAC-AGA-GCA-AT-3'

A wide variety of labels and labeling procedures are suitable for LPE reactions. In addition to fluorescent dyes that are today's standard label, microspheres containing large numbers of attached dye molecules, radioactive labels, mass labels including isotopic mass labels, bioluminescent labels, or chemiluminescent labels can be used. Methods of incorporating the labels include the use of labeled dNTPs, labeled ddNTP, or a combination of these methods can be used. Some labels will interfere with the extension reaction and these labels can be incorporated on the 5'-end of the LPE primers. Labeling is also possible by using post-extension chemical reactions known to those skilled in the art. In the example shown in FIG. 1, a dye label is incorporated into the dideoxythymidylate using standard techniques [Kuppuswamy, et al., *Proc. Natl. Acad. Sci. USA* 88:1143 (1991)] so that there is exactly one label per extension product, thus making quantitative analysis possible. This label is indicated by the asterisk on the thymine at the end of the extension product in FIG. 1A.

Figure 2:
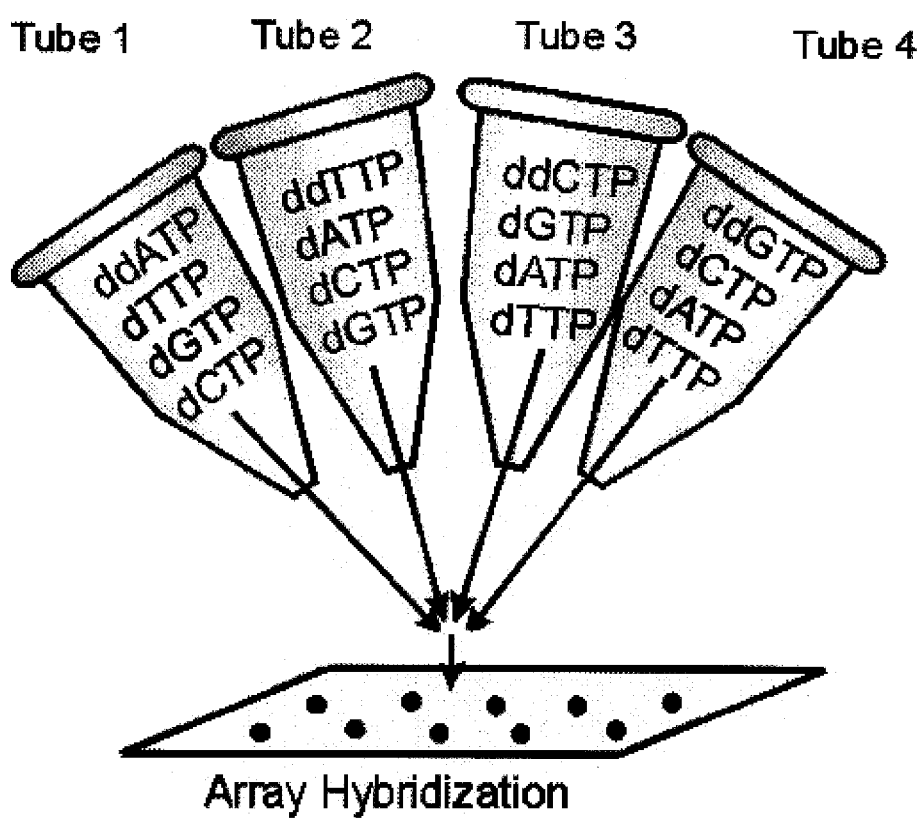
FIG. 2 shows the four reaction sets of nucleotides each with a different dideoxy form used with the invention along with hybridization to an array of immobilized probes. For coverage of all targeted LPE target sequences, the LPE reaction is run in a set of four tubes. Each tube contains an aliquot of the sample DNA, a thermal stable polymerase, three deoxynucleoside triphosphates with the fourth terminating nucleotide either in the dideoxy form or having a 3' end blocking group, and additional components that facilitate optimized LPE reaction performance. Thermal cycles can be used to amplify the LPE product. Then the LPE products are hybridized to immobilized probes that are complementary to at least a portion of the LPE product.

This example of the extension reaction gave an example for only one target sequence. However, one of the strengths of the invention is the ability to multiplex assays for a large number of sequences using only four reaction tubes (FIG. 2). In the preferred embodiment, each tube contains the dideoxy form of a different nucleotide. In addition, each tube contains sample DNA, nucleoside triphosphates for the other three nucleotides, a thermal stable polymerase, and additional components that establish a set of conditions for LPE. The extension reaction may be repeated many times using a thermal-cycling program or helicases to yield short, labeled extension products that are proportional in copy-number to the starting target sequence content of the test sample. Note that because the extension reaction only creates products in one direction (as opposed to the PCR), there are no reaction products that compete with the immobilized probes for association with the extension products. Although the target DNA itself can associate with the product, thermal cycling will create an excess of the extension product.

In the second step, primer extension products are hybridized with an array of complementary oligonucleotide probes. FIG. 1B shows a specific example wherein the probe consists of the 16-base extension complement sequence. More generally, the probe sequence in the invention must be a subset of the sequence that is made up of the ECS and can include several bases on either side of the ECS.

Because all of the primers are introduced into the labeling reaction in identical concentrations, and because the extension reaction results in a nearly linear increase in the number of labeled extension products formed, the resulting hybridization signal is proportional to the number of target sequence copies. Mis-primed extension products do not generate a signal on the microarray because the immobilized probes are only complementary to specific extension products. Quantitative interpretation of hybridization signal intensity can be achieved by using DNA standards.

The array of immobilized probes may be on a solid flat surface such as glass so that the hybridization results can be recovered using a fluorescent microarray scanner. Alternatively, the probes may be immobilized onto fluorescent microbeads where a two-color assessment of the hybridization response is used. Microbead arrays consist of particles that are color coded to identify the gene probe that is present on the bead. A second fluorescent measurement is used to identify and quantify the fluorescent signal achieved from hybridization with the target sequence; in this case, the LPE reaction product. Because both the primer annealing and extension must be specific to generate a hybridization product on the microarray, the total length of the LPE product including primer sequence and extension product may be considered as components that yield specificity. For example, an 18 base primer is used to generate an 18 base extension sequence yielding a total of 36 bases of specific nucleic acid sequence required to generate a hybridization response on the array.

EXAMPLES OF THE INVENTION

Example of an LPE System for Detection of an Enterotoxin Gene

At least 18 probe sequences with 16 or more contiguous bases that lack one of the four nucleotides in a 1612-bp segment of the Bacteriophage 933W slt-II gene emb|X07865.1| encoding the Shiga-like toxin type II subunits A and B (Table 1) were identified. These sequences included one 32-base stretch (no C), one 25-base stretch (no A), two 24-base stretches (no A and no G respectively), one 22-base stretch (no G), three 20-base stretches (no A, no T, and no C respectively), two 19-base stretches (no G and no C respectively), one 18-base (no G), four 17-base stretches (no T, no A, no C, and no G respectively), and three 16-base stretches (no T, no G, and no A respectively). Discounting the low (G+C) sequences (those with less than 40% (G+C)) for either primer sequences or the extension product eliminated nine of the candidate sequences, leaving 9 potential DNA probe sequences. Because either strand of dsDNA are targets for the analysis an additional 9 probe and primer sets can be constructed to target the complementary strand for a total of 18 DNA probe systems for this gene. An additional 11 sites were identified as suitable for peptide nucleic acid (PNA) 12-mer to 15-mer probes [Wang, et al., *Biosensors. J. Am. Chem. Soc.* 118:7667 (1996)] making possible an additional 22 candidate primer/probe sets.

TABLE 1

Primer and Probe Sequences for Bacteriophage 933W slt-II gene emb|X07865.1|

| I.D. | Primer Sequence[a] | Extension Sequence[b] | Probe Sequence | Nucleotide Mix[c] |
|---|---|---|---|---|
| 25F | 5'-ctg-cat-tat-gcg-ttg-tta-gct-3' (SEQ ID NO:2) | 5'-cag-ccg-gac-aga-gca-a-3' (SEQ ID NO:4) | 5'-ttg-ctc-tgt-ccg-gct-g-3' (SEQ ID NO:1) | d(ACG)TP, ddTTP |
| 105F | 5'-cgc-gcc-ata-ttt-att-tac-ca-3' (SEQ ID NO:5) | 5'-ggc-tcg-ctt-ttg-cgg-cct-3' (SEQ ID NO:6) | 5'-agg-ccg-caa-aag-cga-gcc-3' (SEQ ID NO:7) | d(CGT)TP, ddATP |
| 158F | 5'-ggg-tct-ggt-gct-gat-tac-tt-3' (SEQ ID NO:8) | 5'-cag-cca-aaa-gga-aca-cc-3' (SEQ ID NO:9) | 5'-ggt-gtt-cct-ttt-ggc-tg-3' (SEQ ID NO:10) | d(ACG)TP, ddTTP |
| 189R | 5'-cct-ttt-ggc-tga-agt-aat-3' (SEQ ID NO:11) | 5'-cag-cac-cag-acc-cgg-cgc-aga-3' (SEQ ID NO:12) | 5'-tct-gcg-ccg-ggt-ctg-gtg-ctg-3' (SEQ ID NO:13) | d(ACG)TP, ddTTP |
| 222F | 5'-ggg-tac-tgt-gcc-tgt-ta-3' (SEQ ID NO:14) | 5'-ctg-ggt-ttt-tct-tcg-gt-3' (SEQ ID NO:15) | 5'-acc-gaa-gaa-aaa-ccc-ag-3' (SEQ ID NO:16) | d(CGT)TP, ddATP |
| 368F | 5'-cca-cat-cgg-tgt-ctg-tta-tt-3' (SEQ ID NO:17) | 5'-aac-cac-acc-cca-ccg-ggc-ag-3' (SEQ ID NO:18) | 5'-ctg-ccc-ggt-ggg-gtg-tgg-tt-3' (SEQ ID NO:19) | d(ACG)TP, ddTTP |
| 426F | 5'-ggg-gac-cac-atc-ggt-gtc-tg-3' (SEQ ID NO:20) | 5'-tta-tta-acc-aca-ccc-cac-c-3' (SEQ ID NO:21) | 5'-ggt-ggg-gtg-tgg-tta-ata-a-3' (SEQ ID NO:22) | d(ACT)TP, ddGTP |
| 883F | 5'-gca-atg-tgc-ttc-cgg-agt-at-3' (SEQ ID NO:23) | 5'-ggg-gag-agg-atg-gtg-t-3' (SEQ ID NO:24) | 5'-aca-cca-tcc-act-ccc-c-3' (SEQ ID NO:25) | d(AGT)TP, ddCTP |
| 986F | 5'-tgc-cat-cat-cag-ggg-cg-3' (SEQ ID NO:26) | 5'-cgt-tct-gtt-cgc-gcc-gtg-3' (SEQ ID NO:27) | 5'-cac-ggc-gcg-aac-aga-acg-3' (SEQ ID NO:28) | d(CGT)TP, ddATP |
| 1050F | 5'-gat-aac-tgg-cga-cag-gcc-tg-3' (SEQ ID NO:29) | 5'-tta-taa-aaa-taa-aca-ata-cat-tat-3' (SEQ ID NO:30) | 5'-ata-atg-tat-tgt-tta-ttt-tta-taa-3' (SEQ ID NO:31) | d(ACT)TP, ddGTP |

[a]Final 18 bases of the primer sequence are shown. Primer sequences may be extended in the 5' direction to achieve equivalence among the $T_d$ values calculated for the primers.
[b]Extension sequences of greater than 18 bases were adjusted to include the 3' terminal 18 bases.
[c]The indicated dideoxynucleoside triphosphate is the identity of the base immediately 3' to the extension product sequence.

A brief examination of other genes including prokaryotic 16S, the eubacterial glnA gene encoding glutamine synthetase, the phoA gene for *Escherichia coli* alkaline phosphatase, and a number of other gene sequences indicates that useful stretches of DNA sequence that lack one of the four nucleotides are a common property of natural DNA sequences. Table 1 shows 10 selected probe systems. For some of the candidate Bacteriophage 933W slt-II gene emb|X07865.1| probes, the primer sequences designed for either the sense strand, or the complementary antisense strand, would have been poor because of low (G+C) content. Probe system 1050F illustrates two potential problems. First, although the thermal dissociation temperature, $T_d$ of the primer sequence is suitable (63° C.), there are five consecutive bases of 3' self-complementarity that could cause excessive dimer formation. Second, the extension product is a low (G+C) sequence. The extension product would likely perform poorly during hybridization because the $T_d$ of the immobilized complementary probe sequence is only 43° C. Rules for primer and probe candidate sequence selection also excluded systems 105F and 883F as good candidate probe systems for the bacteriophage 933W slt-II gene emb|X07865.1|. The calculated $T_d$ for the remaining seven primer/probe systems ranged from 52° C. to 72° C. and these systems are suitable for empirical testing and length modification.

Discrimination in the LPE system relies on three factors: (1) selectivity of primer annealing to the target, (2) selectivity of the extension product during hybridization with the immobilized probe, and (3) multiple probes for each targeted gene.

We claim:

1. A limited primer extension (LPE) reaction used to produce short DNA extension products from a targeted template nucleic acid which comprises:
    annealing a primer consisting of DNA to a site adjacent to the 3' end of an extension complement sequence (ECS) in the targeted template DNA, which lacks one or more of the four nucleotides over a span of 18 or more contiguous nucleotides;
    generating extension products having a primer portion and an extension portion, said extension portion being complementary to the ECS;
    terminating the extension reaction by either
    i) including only the three deoxyribonucleotides (dNTP) that are complementary to the nucleotides present in said ECS, such that the extension reaction stops at the first occurrence of the nucleotide in the targeted template DNA, which is lacking in the ECS or
    ii) by incorporation of a nucleotide analog that is complementary to the nucleotide absent in the ECS and incapable of supporting further extension;
    dissociating the extension products from the targeted template DNA by varying stringency conditions or with DNA helicases; and
    identifying the extension products by hybridization to a probe immobilized onto a surface followed by detection of the extension product associated to the probe; said probe having sequence identical to, or a subset of, or a superset of, a sequence in the target that includes the ECS.

2. The process of claim 1, wherein the extension reaction product is labeled using a method selected from the group consisting of:
    a) incorporation of labeled nucleotides during the extension reaction,
    b) terminal incorporation of a labeled dideoxy nucleotide,
    c) use of a labeled primer, and
    d) use of aminoallyl chemistries.

3. The process of claim 1, wherein resolution of LPE reaction products is achieved by hybridization to probes with the same sequence as the ECS in the sample.

4. The process of claim 1, wherein resolution of LPE reaction products is achieved by hybridization to probes with a sequence that includes at least a portion of the ECS in the sample.

5. The process of claim 1, wherein resolution of LPE reaction products is achieved by hybridization to probes with a sequence that includes at least a portion of the ECS in the sample and at least a portion of the primer complement.

6. The process of claim 1, wherein resolution of LPE reaction products is achieved by hybridization to probes consisting of a DNA analogue, such as PNA or LNA.

7. The process of claim 1, wherein the nucleic acid template for the LPE reaction contains DNA or RNA.

8. The process of claim 1, wherein extension is terminated by incorporation of a dideoxynucleotide or other modified nucleotide incapable of supporting extension.

9. The process of claim I, wherein extension is effectively terminated by the absence of the dNTP is required to incorporate the nucleotide that is complementary to the nucleotide that is absent in the ECS region of the template DNA.

10. The process of claim 1, wherein thermal cycling us used to generate multiple LPE reaction products from a template by repeated rounds of primer association, extension and dissociation.

11. The process of claim 1, wherein one or more helicases are used to separate the LPE product from the template DNA.

12. The process of claim 11, wherein primer association, extension, and helicase separation of the LPE product from the template DNA are performed at a single temperature.

13. The claim in 11, wherein the helicase is a thermal-stable helicase that remains active at elevated temperatures.

14. The process of claim 1, wherein a DNA thermal-stable polymerase is used to generate the extension product.

15. The process of claim 1, wherein the substrate for hybridization is selected from glass, nylon, or Teflon.

16. The process of claim 1, wherein a chemical process is used to immobilize the probes.

17. The process of claim 1, wherein a microfluidic system is used to locate hybridization products using a microsphere bead array system.

18. The process of claim 2, wherein the label is attached to the 5' end of the LPE primer.

19. The process of claim 2, wherein any part of the LPE primer is labeled prior to use in the LPE reaction.

20. The process of claim 2, wherein the label is incorporated during extension.

21. The process of claim 2, wherein the 3' terminating nucleotide or nucleotide analogue is labeled.

22. The process of claim 2, wherein the LPE product is post-labeled using a chemical method.

23. The process of claim 2, wherein the label is selected from: fluorescent moieties, radioactive moieties, mass labels, isotopic labels, bioluminescent labels, and/or chemiluminescent labels.

24. The process of claim 17, wherein the microsphere bead array system is a Luminex xMAP system.

* * * * *

SEQUENCE LISTING

```
<160> NUMBER OF SEQ ID NOS: 32

<210> SEQ ID NO 1
<211> LENGTH: 16
<212> TYPE: DNA
<213> ORGANISM: Artificial Sequence
<220> FEATURE:
<223> OTHER INFORMATION: Extension Complement Sequence.  Segement void
      of "A". Probe Sequence 25F for Bacteriophage 933W slt-II gene
      embX07865.1

<400> SEQUENCE: 1
ttgctctgtc cggctg                                                    16

<210> SEQ ID NO 2
<211> LENGTH: 21
<212> TYPE: DNA
<213> ORGANISM: Artificial Sequence
<220> FEATURE:
<223> OTHER INFORMATION: Primer directed to segment void of "A".  Primer
      Sequence 25F for Bacteriophage 933W slt-II gene embX07865.1

<400> SEQUENCE: 2
ctgcattatg cgttgttagc t                                              21

<210> SEQ ID NO 3
<211> LENGTH: 38
<212> TYPE: DNA
<213> ORGANISM: Artificial Sequence
<220> FEATURE:
<223> OTHER INFORMATION: Final extension product which includes the
      primer and the extension.

<400> SEQUENCE: 3
ctgcattatg cgttgttagc tcagccggac agagcaat                            38

<210> SEQ ID NO 4
<211> LENGTH: 16
<212> TYPE: DNA
<213> ORGANISM: Artificial Sequence
<220> FEATURE:
<223> OTHER INFORMATION: Extension Sequence 25F for Bacteriophage 933W
      slt-II gene embX07865.1

<400> SEQUENCE: 4
cagccggaca gagcaa                                                    16

<210> SEQ ID NO 5
<211> LENGTH: 20
<212> TYPE: DNA
<213> ORGANISM: Artificial Sequence
<220> FEATURE:
<223> OTHER INFORMATION: Primer Sequence 105F for Bacteriophage 933W
      slt-II gene embX07865.1

<400> SEQUENCE: 5
```

```
cgcgccatat ttatttacca                                               20
```

<210> SEQ ID NO 6
<211> LENGTH: 18
<212> TYPE: DNA
<213> ORGANISM: Artificial Sequence
<220> FEATURE:
<223> OTHER INFORMATION: Extension Sequence 105F for Bacteriophage 933W
      slt-II gene embX07865.1

<400> SEQUENCE: 6

```
ggctcgcttt tgcggcct                                                 18
```

<210> SEQ ID NO 7
<211> LENGTH: 18
<212> TYPE: DNA
<213> ORGANISM: Artificial Sequence
<220> FEATURE:
<223> OTHER INFORMATION: Probe Sequence 105F for Bacteriophage 933W
      slt-II gene embX07865.1

<400> SEQUENCE: 7

```
aggccgcaaa agcgagcc                                                 18
```

<210> SEQ ID NO 8
<211> LENGTH: 20
<212> TYPE: DNA
<213> ORGANISM: Artificial Sequence
<220> FEATURE:
<223> OTHER INFORMATION: Primer Sequence 158F for Bacteriophage 933W
      slt-II gene embX07865.1

<400> SEQUENCE: 8

```
gggtctggtg ctgattactt                                               20
```

<210> SEQ ID NO 9
<211> LENGTH: 17
<212> TYPE: DNA
<213> ORGANISM: Artificial Sequence
<220> FEATURE:
<223> OTHER INFORMATION: Extension Sequence 158F for Bacteriophage 933W
      slt-II gene embX07865.1

<400> SEQUENCE: 9

```
cagccaaaag gaacacc                                                  17
```

<210> SEQ ID NO 10
<211> LENGTH: 17
<212> TYPE: DNA
<213> ORGANISM: Artificial Sequence
<220> FEATURE:
<223> OTHER INFORMATION: Probe Sequence 158F for Bacteriophage 933W
      slt-II gene embX07865.1

<400> SEQUENCE: 10

```
ggtgttcctt ttggctg                                                  17
```

<210> SEQ ID NO 11
<211> LENGTH: 18
<212> TYPE: DNA
<213> ORGANISM: Artificial Sequence
<220> FEATURE:
<223> OTHER INFORMATION: Primer Sequence 189R for Bacteriophage 933W
      slt-II gene embX07865.1

<400> SEQUENCE: 11

```
ccttttggct gaagtaat                                                       18
```

<210> SEQ ID NO 12
<211> LENGTH: 21
<212> TYPE: DNA
<213> ORGANISM: Artificial Sequence
<220> FEATURE:
<223> OTHER INFORMATION: Extension Sequence 189R for Bacteriophage 933W
      slt-II gene embX07865.1

<400> SEQUENCE: 12

```
cagcaccaga cccggcgcag a                                                   21
```

<210> SEQ ID NO 13
<211> LENGTH: 21
<212> TYPE: DNA
<213> ORGANISM: Artificial Sequence
<220> FEATURE:
<223> OTHER INFORMATION: Probe Sequence 189R for Bacteriophage 933W
      slt-II gene embX07865.1

<400> SEQUENCE: 13

```
tctgcgccgg gtctggtgct g                                                   21
```

<210> SEQ ID NO 14
<211> LENGTH: 17
<212> TYPE: DNA
<213> ORGANISM: Artificial Sequence
<220> FEATURE:
<223> OTHER INFORMATION: Primer Sequence 222F for Bacteriophage 933W
      slt-II gene embX07865.1

<400> SEQUENCE: 14

```
gggtactgtg cctgtta                                                        17
```

<210> SEQ ID NO 15
<211> LENGTH: 17
<212> TYPE: DNA
<213> ORGANISM: Artificial Sequence
<220> FEATURE:
<223> OTHER INFORMATION: Extension Sequence 222F for Bacteriophage 933W
      slt-II gene embX07865.1

<400> SEQUENCE: 15

```
ctgggttttt cttcggt                                                        17
```

<210> SEQ ID NO 16
<211> LENGTH: 17
<212> TYPE: DNA
<213> ORGANISM: Artificial Sequence
<220> FEATURE:
<223> OTHER INFORMATION: Probe Sequence 222F for Bacteriophage 933W
      slt-II gene embX07865.1

<400> SEQUENCE: 16

```
accgaagaaa aacccag                                                        17
```

<210> SEQ ID NO 17
<211> LENGTH: 20
<212> TYPE: DNA
<213> ORGANISM: Artificial Sequence
<220> FEATURE:
<223> OTHER INFORMATION: Primer Sequence 368F for Bacteriophage 933W
      slt-II gene embX07865.1

<400> SEQUENCE: 17

```
ccacatcggt gtctgttatt                                                     20
```

-continued

<210> SEQ ID NO 18
<211> LENGTH: 20
<212> TYPE: DNA
<213> ORGANISM: Artificial Sequence
<220> FEATURE:
<223> OTHER INFORMATION: Extension Sequence 368F for Bacteriophage 933W
      slt-II gene embX07865.1

<400> SEQUENCE: 18
aaccacaccc caccgggcag                                              20

<210> SEQ ID NO 19
<211> LENGTH: 20
<212> TYPE: DNA
<213> ORGANISM: Artificial Sequence
<220> FEATURE:
<223> OTHER INFORMATION: Probe Sequence 368F for Bacteriophage 933W
      slt-II gene embX07865.1

<400> SEQUENCE: 19
ctgcccggtg gggtgtggtt                                              20

<210> SEQ ID NO 20
<211> LENGTH: 20
<212> TYPE: DNA
<213> ORGANISM: Artificial Sequence
<220> FEATURE:
<223> OTHER INFORMATION: Primer Sequence 426F for Bacteriophage 933W
      slt-II gene embX07865.1

<400> SEQUENCE: 20
ggggaccaca tcggtgtctg                                              20

<210> SEQ ID NO 21
<211> LENGTH: 19
<212> TYPE: DNA
<213> ORGANISM: Artificial Sequence
<220> FEATURE:
<223> OTHER INFORMATION: Extension Sequence 426F for Bacteriophage 933W
      slt-II gene embX07865.1

<400> SEQUENCE: 21
ttattaacca caccccacc                                               19

<210> SEQ ID NO 22
<211> LENGTH: 19
<212> TYPE: DNA
<213> ORGANISM: Artificial Sequence
<220> FEATURE:
<223> OTHER INFORMATION: Probe Sequence 426F for Bacteriophage 933W
      slt-II gene embX07865.1

<400> SEQUENCE: 22
ggtggggtgt ggttaataa                                               19

<210> SEQ ID NO 23
<211> LENGTH: 20
<212> TYPE: DNA
<213> ORGANISM: Artificial Sequence
<220> FEATURE:
<223> OTHER INFORMATION: Primer Sequence 883F for Bacteriophage 933W
      slt-II gene embX07865.1

<400> SEQUENCE: 23
gcaatgtgct tccggagtat                                              20

```
<210> SEQ ID NO 24
<211> LENGTH: 16
<212> TYPE: DNA
<213> ORGANISM: Artificial Sequence
<220> FEATURE:
<223> OTHER INFORMATION: Extension Sequence 883F for Bacteriophage 933W
      slt-II gene embX07865.1

<400> SEQUENCE: 24
ggggagagga tggtgt                                                     16

<210> SEQ ID NO 25
<211> LENGTH: 16
<212> TYPE: DNA
<213> ORGANISM: Artificial Sequence
<220> FEATURE:
<223> OTHER INFORMATION: Probe Sequence 883F for Bacteriophage 933W
      slt-II gene embX07865.1

<400> SEQUENCE: 25
acaccatcca ctcccc                                                     16

<210> SEQ ID NO 26
<211> LENGTH: 17
<212> TYPE: DNA
<213> ORGANISM: Artificial Sequence
<220> FEATURE:
<223> OTHER INFORMATION: Primer Sequence 986F for Bacteriophage 933W
      slt-II gene embX07865.1

<400> SEQUENCE: 26
tgccatcatc agggcg                                                     17

<210> SEQ ID NO 27
<211> LENGTH: 18
<212> TYPE: DNA
<213> ORGANISM: Artificial Sequence
<220> FEATURE:
<223> OTHER INFORMATION: Extension Sequence 986F for Bacteriophage 933W
      slt-II gene embX07865.1

<400> SEQUENCE: 27
cgttctgttc gcgccgtg                                                   18

<210> SEQ ID NO 28
<211> LENGTH: 18
<212> TYPE: DNA
<213> ORGANISM: Artificial Sequence
<220> FEATURE:
<223> OTHER INFORMATION: Probe Sequence 986F for Bacteriophage 933W
      slt-II gene embX07865.1

<400> SEQUENCE: 28
cacggcgcga acagaacg                                                   18

<210> SEQ ID NO 29
<211> LENGTH: 20
<212> TYPE: DNA
<213> ORGANISM: Artificial Sequence
<220> FEATURE:
<223> OTHER INFORMATION: Primer Sequence 1050F for Bacteriophage 933W
      slt-II gene embX07865.1

<400> SEQUENCE: 29
gataactggc gacaggcctg                                                 20
```

-continued

```
<210> SEQ ID NO 30
<211> LENGTH: 24
<212> TYPE: DNA
<213> ORGANISM: Artificial Sequence
<220> FEATURE:
<223> OTHER INFORMATION: Extension Sequence 1050F for Bacteriophage 933W
      slt-II gene embX07865.1

<400> SEQUENCE: 30
ttataaaaat aaacaataca ttat                                              24

<210> SEQ ID NO 31
<211> LENGTH: 24
<212> TYPE: DNA
<213> ORGANISM: Artificial Sequence
<220> FEATURE:
<223> OTHER INFORMATION: Probe Sequence 1050F for Bacteriophage 933W
      slt-II gene embX07865.1

<400> SEQUENCE: 31
ataatgtatt gtttattttt ataa                                              24

<210> SEQ ID NO 32
<211> LENGTH: 38
<212> TYPE: DNA
<213> ORGANISM: Artificial Sequence
<220> FEATURE:
<223> OTHER INFORMATION: Complete complement sequence.

<400> SEQUENCE: 32
attgctctgt ccggctgagc taacaacgca taatgcag                               38
```